(12) United States Patent
Yang et al.

(10) Patent No.: US 11,255,859 B2
(45) Date of Patent: Feb. 22, 2022

(54) USE OF HEXOKINASE-2 IN DETECTION OF RARE TUMOR CELLS IN BODY FLUID SAMPLE AND KIT

(71) Applicant: Suzhou Junhui Biotechnology Co., Ltd., Jiangsu (CN)

(72) Inventors: Liu Yang, Shanghai (CN); Yingqi Hua, Shanghai (CN); Zhengdong Cai, Shanghai (CN)

(73) Assignee: SUZHOU JUNHUI BIOTECHNOLOGY CO., LTD., Jiangsu (CN)

(*) Notice: Subject to any disclaimer, the term of this patent is extended or adjusted under 35 U.S.C. 154(b) by 0 days.

(21) Appl. No.: 17/103,190

(22) Filed: Nov. 24, 2020

(65) Prior Publication Data

US 2021/0080468 A1 Mar. 18, 2021

Related U.S. Application Data

(63) Continuation of application No. PCT/CN2019/099780, filed on Aug. 8, 2019.

(51) Int. Cl.
*G01N 33/574* (2006.01)
*G01N 33/569* (2006.01)

(52) U.S. Cl.
CPC . *G01N 33/57492* (2013.01); *G01N 33/56966* (2013.01); *G01N 2333/91215* (2013.01)

(58) Field of Classification Search
None
See application file for complete search history.

(56) References Cited

FOREIGN PATENT DOCUMENTS

| CN | 105063165 | 11/2015 |
|---|---|---|
| CN | 105331516 A | 2/2016 |
| CN | 105954246 A | 9/2016 |
| CN | 107674861 A | 2/2018 |
| CN | 107917869 A | 4/2018 |
| WO | 20150095603 A1 | 6/2015 |

OTHER PUBLICATIONS

Ho et al (CTT, 6:11-16, 2016).*
Liang et al (ACA, 1044:93-101, 2018).*
Patra et al (CC, 24(2):213-228, 2013).*
Li et al (CS, 105(8):951-955, 2014).*
Li et al (TB, 1-9, 2017).*
International Search Report and Written Opinion for PCT/CN2019/099780 dated Dec. 31, 2019, with English translation, 9 pages.

* cited by examiner

*Primary Examiner* — Brad Duffy

(74) *Attorney, Agent, or Firm* — Sheppard Mullin Richter & Hampton LLP

(57) ABSTRACT

The present application relates to use of hexokinase-2 and a kit for detecting rare tumor cells in body fluid sample. The present application, based on a principle of abnormal tumor cell energy metabolism, conducts a vitro detection by using a glycolysis marker hexokinase-2 (HK2) as a marker, and assists localization and selection of the rare tumor cells by an addressable microporous array chip or a glass sheet, so as to implement a detection on rare tumor cells having high glycolysis activity in a cancer patient's body fluid sample. The detection method of present application allows to detect rare tumor cells having high glycolysis activity in the human body fluid sample, especially detect circulating tumor cells of an interstitial origin tumor and the circulating tumor cells having epithelial-interstitial transformation in epithelial origin tumors, thereby covering the shortage of traditional detection against the circulating tumor cells based on an epithelial marker, and providing a technical basis for better application of cancer liquid biopsy in clinic.

4 Claims, 11 Drawing Sheets

USE OF HEXOKINASE-2 IN DETECTION OF RARE TUMOR CELLS IN BODY FLUID SAMPLE AND KIT

CROSS-REFERENCE TO RELATED APPLICATIONS

This application is a continuation of International Application No. PCT/CN2019/099780, filed Aug. 8, 2019, which claims priority to CN 201910285242.2, filed Apr. 10, 2019, the contents of which are incorporated to the present disclosure by reference.

TECHNICAL FIELD

The present application relates to the field of biological and medical detection. More particularly, the present application relates to method for detecting rare tumor cells in human body fluid sample (such as blood, cerebrospinal fluid, hydrothorax, urine and the like).

BACKGROUND

Cancer has high incidence rate and fatality rate around the world, it has seriously threatened the human health. Liquid biopsy is a new technique for non-invasive tumor detection which appeared in recent years. High metastasis capacity of tumor cells causes them to abscise from in situ tumor focus, and further disseminate and migrate towards body fluid including blood, hydrothorax, cerebrospinal fluid even urine. Detecting free rare tumor cells and molecular characteristics thereof from these liquid sample can replace biopsy on in situ tumor focus, thus it is referred to as liquid biopsy. Because the traditional biopsy has big trauma and it is often difficult to conduct, the liquid biopsy, especially the liquid biopsy against blood is welcomed by the clinic, because it is non-invasive and easy to obtain a sample. However, its technical difficulty primarily lies in how to confirm that a certain free cell in the liquid sample is really a tumor cell. At present, a gold standard for identifying a malignant tissue in clinic is based on morphological characteristics in pathology. This method can also be used in identifying exfoliated tumor cells in a liquid sample (such as hydrothorax, cerebrospinal fluid, urine and the like), but the cellular constituents in the liquid sample are complex, and there exist a large amount of cells which are similar to the tumor cells in morphology and easily confusable (such as reactive mesothelial cell in hydrothorax), meanwhile the number of the tumor cells maybe small, therefore it is often difficult to draw a definite conclusion, resulting in low sensitivity of detection for the malignant cells in the liquid sample. In blood, the number of the circulating tumor cells is very few, and the number of other cells is very large (up to $10^9$), thus it is more difficult to accurately detect by a morphological method.

At present, in market and academia, there are various different techniques and equipments for detecting circulating tumor cells (CTC) in blood, but the core CTC identification standard essentially adopts the method used by CellSearch system of Johnson & Johnson Company approved by US FDA in which an epithelial marker is combined with a leucocyte marker, namely the cells which are EpCAM+/CK+/CD45−/DAPI+ and meet a certain morphological standard are defined as CTC, wherein EpCAM and CK (cytokeratin) are both epithelial marker, CD45 is leucocyte marker, and DAPI is nuclear marker. Therefore, the above-mentioned definition mainly depends on the epithelial marker, because most of the tumors are of epithelial origin, but this standard cannot detect CTC of a tumor having interstitial origin (such as osteosarcoma, melanoma and the like) and CTC having epithelial-interstitial transformation in an tumor having epithelial origin. According to the existing biological theory of cancer, EMT is an important step in tumor cell metastasis, thus the tumor cells transformed from epithelial type to interstitial type are closely related to the tumor metastasis, and this part of tumor cells are difficult to be detected by the epithelial marker. Accordingly, this promotes we to develop a new CTC marker capable of more sensitively detecting CTC, especially CTC of a tumor having interstitial origin and CTC of a tumor having epithelial origin which does not express the epithelial marker (such as CK). We primarily search for a new CTC marker on the basis of general characteristics of cancer.

Cancer has a big harm and is hard to conquer, this is because a malignant tumor cell has several characteristics different from a normal cell, including self-sufficiency in growth signals, insensitivity to antigrowth signals, resisting cell death, limitless replicative potential, sustained angiogenesis, tissue invasion and metastasis, avoiding immune destruction, tumor promotion inflammation, deregulating cellular energetics as well as genome instability and mutation etc. (See Douglas Hanahan, Robert A. Weinberg, "Hallmarks of Cancer: The Next Generation", Cell, 2011, vol. 144, p646-674). Wherein abnormal energy metabolism of the tumor cell, as one of main indicators for cancer, receives more and more attentions, it provides tumor detection and therapy with new method and target. The tumor cells use glycolysis as their main source of energy metabolism, even under an aerobic circumstance they also uptake a large amount of glucose, such phenomenon is referred to as Warburg effect, it is one of the basic characteristics of tumor. Otto Warburg accordingly won the Nobel prize of 1931.

We know that glycolysis is a cascade reaction process catalyzed by a series of enzymes, a first key rate-limiting enzyme which catalyzes glycolysis is hexokinases (HKs). HK catalyzes phosphorylation of glucose entering into the cell to generate glucose-6-phosphate (G-6-P), and consumes one molecule of ATP. Now it has been found that human HK has four subtypes, which are respectively encoded and generated by HK1, HK2, HK3 and HK4 genes. HK1 is widely expressed in almost all mammalian tissues, HK2 is generally expressed in a insulin sensitive tissue such as fat, skeleton and myocardium. HK3 tends to be expressed at a low level. The expression of HK4 is limited to pancreas and liver. Reports and studies using a kinase (such as HK) as the marker for identifying rare tumor cells in a human liquid sample have not been seen.

SUMMARY

The present application provides a method for detecting rare tumor cells in a cancer patient's liquid sample, a detection kit, and use of HK2 antibody substance, to solve the issue of the existing method based one epithelial marker namely being unable to detect CTC of the tumor having interstitial origin and CTC having epithelial-interstitial transformation of the tumor having epithelial origin, and to further increase the detection sensitivity of CTC.

A first aspect of the present application provides a method for detecting rare tumor cells in the human body fluid sample, comprising: conducting a staining treatment on cells from the human body fluid sample with a fluorescein labeled hexokinase-2 (HK2) antibody substance, and conducting a fluorescence detection on the cells after the staining treatment; and confirming HK2 positive cell and cells with high HK2 levels cell as the rare tumor cells according to a fluorescence signal.

In the above-mentioned method for detecting rare tumor cells in the human body fluid sample, as one preferred regime, mean value of HK2 fluorescence values of all leucocyteas at the time of fluorescence detection plus five folds of a standard deviation is regarded as a threshold for determining cells with high HK2 levels.

In the above-mentioned method for detecting rare tumor cells in the human body fluid sample, as one preferred regime, it also comprises conducting a staining treatment on the cells from the body fluid sample with a fluorescein labeled antibody targeting the leukocyte marker, and conducting a staining treatment on the cells from the human body fluid sample with a cell nucleus stain, the cells which accord with cells with high HK2 levels/leucocyte marker negative/cell nucleus staining positive are rare tumor cells.

In the above-mentioned method for detecting rare tumor cells in the human body fluid sample, as one preferred regime, a fluorescein labeled HK2 antibody substance is a fluorescein labeled Anti-HK2 antibody, or a combination of an Anti-HK2 antibody with a fluorescein labeled secondary antibody targeting HK2 primary antibody.

In the above-mentioned method for detecting rare tumor cells in the human body fluid sample, as one preferred regime, said leucocyte marker antibody is an antibody against cell membrane surface protein CD45, said nuclear stain is a fluorescent dye targeting cell nucleus. Mean value of HK2 fluorescence value plus five times of standard deviation of CD45 positive cells is defined as a threshold for determining cells with high HK2 levels.

In the above-mentioned method for detecting rare tumor cells in the human body fluid sample, as one preferred regime, said human body fluid sample is blood, hydrothorax, cerebrospinal fluid or urine samples, after conducting an selective enrichment treatment on said body fluid sample, the cells are prepared into a cell suspension, and spread in a form of single cell onto an addressable microporous array chip or a glass sheet to conduct a staining treatment, said enrichment treatment comprises decreasing the number of erythrocyte and/or leucocyte in the human body fluid sample.

In the above-mentioned method for detecting rare tumor cells in the human body fluid sample, as one preferred regime, it also comprises the following steps: (a) conducting a pre-treatment and an enrichment on the human body fluid sample; (b) dispersing all the cells in the sample after enrichment onto the addressable microporous array chip or the glass sheet; (c) conducting a fluorescent staining and an imaging based on the marker for all the cells on the microporous array chip or the glass sheet; (d) recognizing a suspected tumor cell according to the threshold of the fluorescence signal or in a manner of artificial intelligence, and counting the number after a manual review; (e) recycling and recognizing the tumor cells by a micromanipulation technique, conducting a single cell sequencing and conducting a validation or detecting the drug target thereof; note: if this step is not required to detect the drug target, it is a non-required step.

A second aspect of the present application provides a kit for detecting rare tumor cells, it includes: a fluorescein labeled HK2 antibody substance, a fluorescein labeled antibody targeting the leukocyte marker, and a cell nucleus stain.

A third aspect of the present application provides a use of the HK2 antibody substance, used in:

a) detecting the rare tumor cells for a non-diagnostic purpose; or
b) preparing a detection kit for rare tumor cells; or
c) serving as a tumor cell marker, detecting rare tumor cells.

In use of the above-mentioned HK2 antibody substance, as one preferred regime, cells with high HK2 levels/leucocyte marker negative/cell nucleus staining positive cell in the human body fluid sample are identified as rare tumor cells; and rare tumor cells of epithelial cell marker negative in the human body fluid sample are identified as the tumor cell having epithelial-interstitial transformation or the tumor cells having interstitial origin; the cell with high HK2 levels referring to a cell in which the fluorescence signal value after the HK2 fluorescent staining treatment reaches a predetermined threshold.

A fourth aspect of the present application provides a combined use of the HK2antibody substance and an epithelial cell marker antibody substance in preparing a detection kit for identifying characteristics of CTC. Said HK2 antibody substance is a fluorescein labeled Anti-HK2 antibody, or a combination of an Anti-HK2 antibody with a fluorescein labeled secondary antibody targeting HK2 primary antibody. Said epithelial cell marker antibody substance is a fluorescein labeled CK antibody. Said characteristics of CTC refers to characteristics for distinguishing CTC cell as a tumor cell having epithelial origin, a tumor cell having epithelial-interstitial transformation, or a tumor cell having interstitial origin. Said kit also includes a fluorescein labeled antibody targeting the leukocyte marker, a nuclear stain, and a instruction. Said instruction records the following contents: confirming the epithelial cell marker positive cell CTC cell as the tumor cell having epithelial origin, confirming the epithelial cell marker negative cell as the tumor cell having epithelial-interstitial transformation, or the tumor cell having interstitial origin.

The present application uses HK2 as a marker, and identify the rare tumor cells with a marker combination of HK2, CD45 (leucocyte marker), DAPI (nuclear dye); this new method can detect CTC of the tumor having interstitial origin which cannot be detected by a traditional epithelial marker and CTC having epithelial-interstitial transformation in the tumor having epithelial origin, so as to increase the detection sensitivity. On the other hand, HK2 is related to the abnormal energy metabolism which is common in tumor, namely high glycolysis, thus it can be used in identifying malignant degree of the cells, so as to ensure specificity of the detection. We also further validate reliability of the suspected tumor cell detected with this new marker by mean of a single cell sequencing.

The method described in the present application can be suitable for various liquid biopsy samples of the cancer patient, including blood, hydrothorax, cerebrospinal fluid, urine and the like; but during implementation of the patent, since the number of total cells contained in different human body fluid samples is different, it is required to adopt different sample enrichment methods. For instance, the number of the cells contained in cerebrospinal fluid is also smallest (less than 100 thousand), thus it is not required to conduct any sample enrichment steps, all the cells in the sample can be directly dispersed onto the addressable microporous array chip or the glass sheet to conduct staining and imaging. The number of the cells in urine is bit more, but generally it is less than one million, thus it is also not required to adopt any enrichment steps. The number of erythrocyte in hydrothorax, especially in bloody hydrothorax is larger, it is required to conduct a simple cell enrichment, namely lysis and removal of erythrocyte, beyond that it is generally not required to further conduct other enrichment steps. The number of the cells in blood is largest (every milliliter of blood contains 5 billion erythrocytes, and several million leucocytes), therefore it is often required to conduct one step or multiple steps of enrichment, for instance a positive selection against a target cell, or removing a non-target cell (such as erythrocyte, leucocyte) by a negative selection, or combining the positive selection with the negative selection. The aforementioned treatment and enrichment on different human body fluid samples as well as staining and imaging against the marker and single cell sequencing and validation are all disclosed in the embodiments.

BRIEF DESCRIPTION OF DRAWINGS

FIG. 4 shows a fluorescent sub-channel diagram of CTC of the lung adenocarcinoma patient related to FIG. 3, according to the expression of HK2 and CK the cells can further divided into three cell subgroups of HK2 positive/CK positive/CD45 negative/DAPI positive, HK2 positive/CK negative/CD45 negative/DAPI positive, and HK2 negative/CK positive/CD45 negative/DAPI positive and the like.

FIG. 9 shows a fluorescent sub-channel diagram of rare tumor cells detected in cerebrospinal fluid of one lung cancer patient, according to the expression of HK2 and CK the rare tumor cells can further divided into three cell subgroups of HK2 positive/CK positive/CD45 negative/DAPI positive, HK2 positive/CK negative/CD45 negative/DAPI positive and HK2 negative/CK positive/CD45 negative/DAPI positive and the like.

DETAILED DESCRIPTION

The present application is further explained below in conjunction with the specific embodiments. It should be understood that, these embodiments are merely used to illustrate the present application but not to limit the scope of the present application. In addition, it should be understood that, after reading the contents recorded in the present application, one skilled in the art can make various alterations or modifications in the present application, these equivalent forms also fall into the scope defined by the appended claims of the present application.

When the present application is not particularly illustrated, technical measures adopted in the following embodiments are conventional technical measure well known to one skilled in the art, and the raw materials and the reagents used in the application are all also commercially available products.

Figure 1:
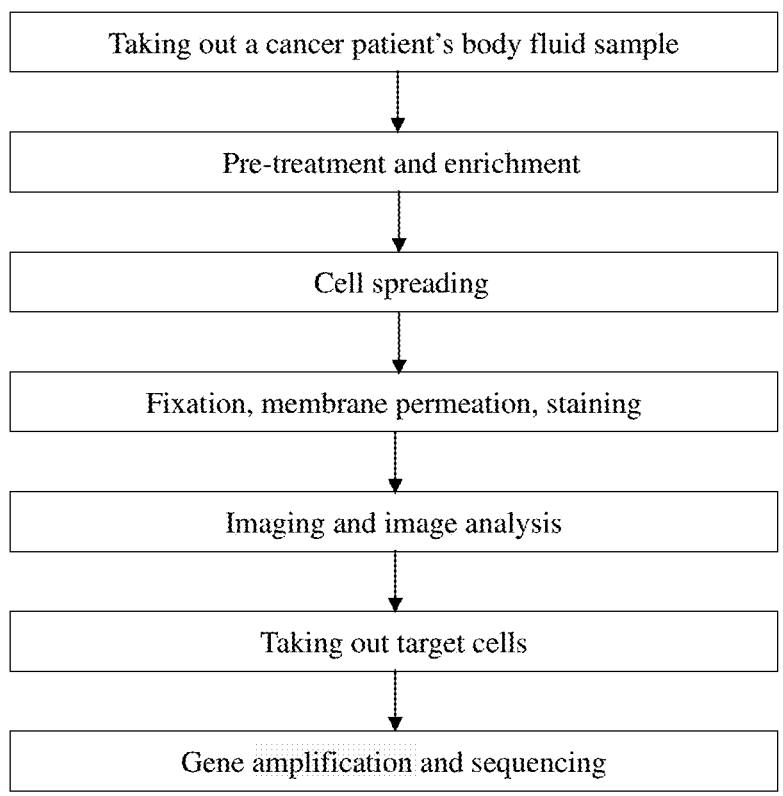
FIG. 1 shows an experimental procedure flow diagram described in the present application.

As shown in FIG. 1, a detecting method for rare tumor cells in said human body fluid (such as blood, cerebrospinal fluid, hydrothorax, urine and the like) sample mainly comprises the following specific steps:

(a) taking a cancer patient's human body fluid sample: under the premise of informed consent of the patient, in accordance with the conventional steps specified in the manual, drawing out the cancer patient's body fluid sample;

(b) pre-treatment and enrichment: because total number of the cells contained in different human body fluid samples are different, it is required to adopt different sample pre-treatment and enrichment methods for different samples.

(c) cell spreading: spreading the cells onto an addressable microporous array chip or a glass sheet;

(d) fixation, permeation, staining of the cells: after fixation and permeation of the cells, conducting a staining treatment to identify the rare tumor cells in the human body fluid, wherein the staining reagent is a fluorescein labeled HK2 antibody substance having a certain concentration, a CD45 antibody substance and a cell nucleus stain DAPI. Note: for a lung adenocarcinoma human body fluid sample etc., adding CK antibody substance having a certain concentration into the staining reagent, in order to compare the HK2 detection result with the typing result based on CK expression;

(e) imaging and image analysis: conducting a fluorescent analysis to preliminarily determine that CD45 negative/DAPI positive/HK2 or CK positive cells are tumor cells, wherein HK2 and CK positive threshold is mean value of leucocyte fluorescence values plus five folds of the standard deviation;

(f) removing a target cell: obtaining the target cell by means of various equipments such as a micromanipulator etc.;

(g) gene amplification and sequencing: conducting a single cell sequencing or other detection methods known in the art for determining rare tumor cells, to confirm that whether they are tumor cells or not.

Wherein said fluorescein labeled HK2/CD45/CK antibody substance is HK2/CD45/CK antibody which is directly labeled with fluorescein or other fluorescent substance (such as quantum dot), or a combination consisting of a non-labeled HK2/CD45/CK primary antibody and a secondary antibody labeled with fluorescein or other fluorescent substance.

Further, in order to reduce or eliminate interference to fluorescent analysis by some non-cellular impurities having adsorption on fluorescein labeled antibody substance of HK2 in the detection sample or being introduced in the treatment process (such as cell debris, bubble, non-cellular particle and the like), the specific embodiment of the present application method also comprises conducting staining on the sample cells by using a nuclear dye e.g. fluorescent dye targeting cell nucleus (DAPI or Hoechst series staining) when, before or after HK2 staining. In this case, the HK2 positive cells which are also cell nucleus staining positive are preliminarily judged as rare tumor cells.

In conclusion, these results suggest that the method has high sensitivity and reliability, it can be used in detecting the rare tumor cells having high glycolysis activity in a lung adenocarcinoma patient's hydrothorax sample, especially it can be used in detecting the rare tumor cells having epithelial-interstitial transformation in an tumor having epithelial origin, and provide the liquid biopsy of cancer with new detection means and important biological information.

A lot of tests shown hereinafter indicates that, for a purpose of detecting the rare tumor cells, it is not required to implement the present application by using the epithelial cell marker (e.g. CK), or the present application is not required to determine whether the sample cell is epithelial cell marker positive or not. The present application can simultaneously detect the tumor cell having epithelial origin, the tumor cell of the epithelial origin tumor having epithelial-interstitial transformation, and the circulating tumor cells of interstitial origin tumor in the sample as the tumor cell, certainly it does not rule out that a part of tumor cell with apoptosis or very low metabolic activity cannot be detected by the present application.

On the other hand, if there is an actual need for distinguishing CTC characteristics, for instance what proportion of the tumor cells in CTC have epithelial-interstitial transformation, in preferred embodiments of the present application HK2 can be used together with CK. In the present application, the detected epithelial cell marker positive cell in the tumor cells can be confirmed as the tumor cell of epithelial origin, and the epithelial cell marker negative cell can be confirmed as the tumor cell having epithelial-interstitial transformation, or the tumor cell of interstitial origin.

The following embodiments particularly discuss the whole process and the analysis result which adopts the above-mentioned detection method to conduct a specific identification on the rare tumor cells in the human body fluid, in order to show validity and superiority of the present application.

Embodiment 1

Detection of CTC in a Lung Adenocarcinoma Patient's Blood Sample

Figure 2:
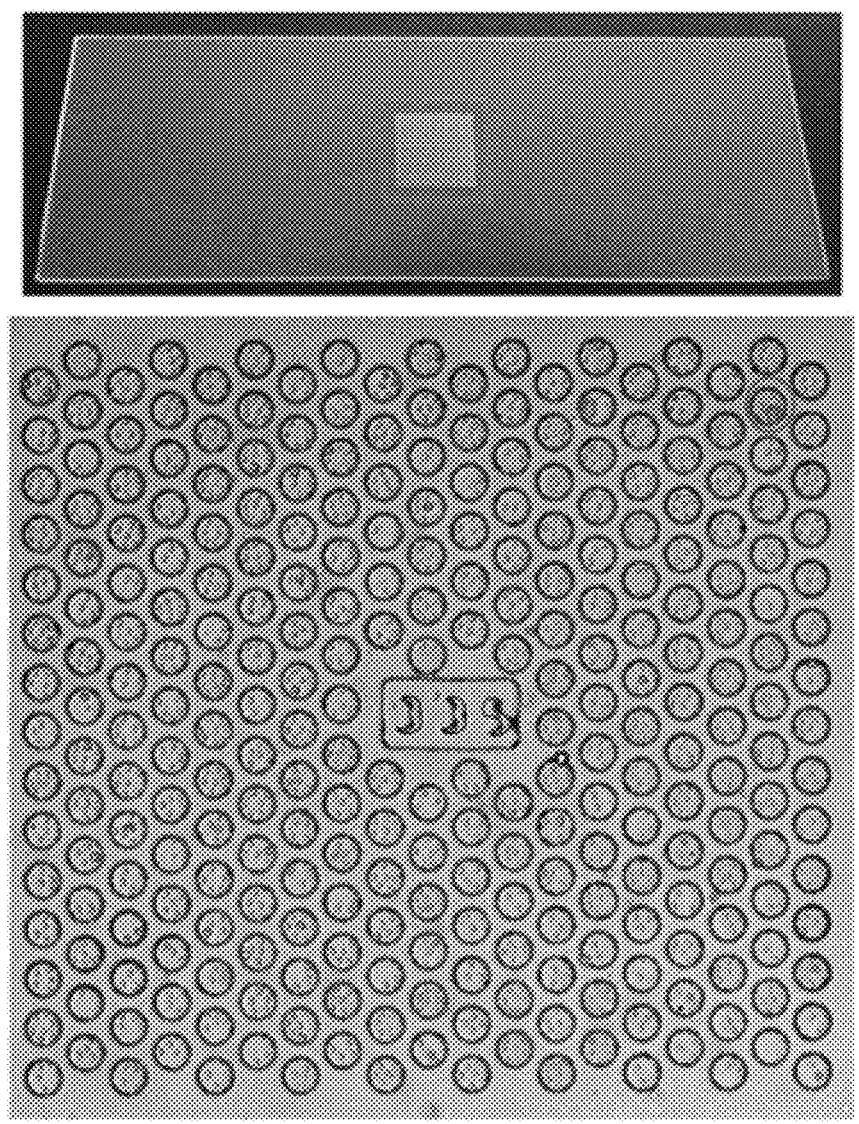
FIG. 2 show a photograph of an addressable microporous array chip described in the present application and an enlarged picture of one numbered area on the ship, a cell can be localized on the basis of location of the cell in the micropore, location of the micropore in the numbered area and number of the area, in order to manipulate and isolate a single cell.

In this embodiment, the specific method comprises the following steps:

(1) into 5 ml of lung cancer patient's peripheral blood, 75 μl of antibody mixed liquor against erythrocyte, leucocyte and platelet antigen (STEMCELL Company) was added, incubated at room temperature for 20 minutes, and 15 ml of Hank's balanced salt solution (HBSS) containing 2% fetal calf serum (FBS) was added, mixed well;

(2) from a hole in a density gradient centrifugal tube (STEMCELL Company) interlayer, 15 ml of density gradient centrifugate (STEMCELL Company) was added, avoiding formation of bubble during the addition;

(3) the mixed liquor at step (1) was added into the density gradient centrifugal tube along the tube wall at step (2), preventing mixing between the layers, after being accurately balanced, centrifuged for 20 minutes (at room temperature, 1200 g, centrifuge braking: acceleration 9, deceleration 6), an uppermost supernatant in the density gradient centrifugal tube was discarded (about 10 ml), then the remaining supernatant (about 10 ml) was poured into a new centrifugal tube in one portion, centrifuged again (at room temperature, 600 g, 8 minutes, centrifuge braking: acceleration 6, deceleration 6), after the supernatant was discarded 1 ml of erythrocyte lysate (BD Company) was added, lysed at room temperature in a dark place for 5 minutes; (4) centrifuged (4° C., 250 g, 5 minutes), most of the supernatant was discarded, the cells were resuspended with the remaining 100 μl liquid, this 100 μl cell suspension was dripped onto the microporous array chip, standing for 30 minutes, a microscopic bright field picture of the chip is as shown in FIG. 2, in this embodiment, the microporous array chip includes 400 numbered areas in total, and includes in total about 140 thousand addressable micropores for accommodating the cells and providing localization for the cells, wherein the diameter of each micropore was 30 μm, the cells were evenly distributed in the chip and sunk into the chip micropores;

(5) the chip surface was washed twice with HBSS, the solution on the chip surface was absorbed, 100 μl of 2% paraformaldehyde (PFA) was added onto the chip and the cells were fixed at room temperature (10 minutes), the chip surface was washed five times with a phosphate buffer (PBS), the solution on the chip surface was absorbed, 30 μl of 0.5% polyethylene glycol octylphenol ether (Triton X-100) was added onto the chip and treated for 15 minutes, to increase permeability of cell membrane to the antibody, the chip surface was washed five times with PBS, the solution on the chip surface was absorbed, 100 μl of mixed liquor of 3% bovine serum albumin (BSA) and 10% goat serum was added onto the chip, and blocked at room temperature for 1 hour;

(6) the chip surface was washed twice with PBS, the solution on the chip surface was absorbed, 100 μl of antibody mixed liquor was added onto the chip: including 1% APC labeled CD45 antibody (source of mouse, Thermo Fisher Company), 1% PE labeled CK antibody (source of mouse, BD Company) and 1% HK2 primary antibody (source of rabbit, Abcam Company), and incubated at 4° C. overnight;

(7) the chip was washed eight times with PBS, the solution on the chip surface was absorbed, 100 μl of mixed liquor of 3% BSA and 10% goat serum was added onto the chip, blocked at room temperature for 1 hour, the chip surface was washed twice with PBS, the solution on the chip surface was absorbed, 100 μl of 0.25% FITC labeled goat anti-rabbit secondary antibody (Thermo Fisher Company) was added onto the chip, incubated at room temperature for 1 hour, the chip was washed five times with PBS, the solution on the chip surface was absorbed, 100 μl of DAPI stock solution was added onto the chip, and incubated at room temperature for 10 minutes, after completion of the incubation the chip was washed five times with PBS;

(8) imaging was conducted by using the high speed fluorescent imaging equipment, and the scanning result was analyzed, wherein HK2 and CK positive threshold was mean value of fluorescence values of leucocyte on the chip plus five folds of the standard deviation. The criteria for CD45 positive and DAPI positive are if a color is developed then it is positive.

Figure 3:
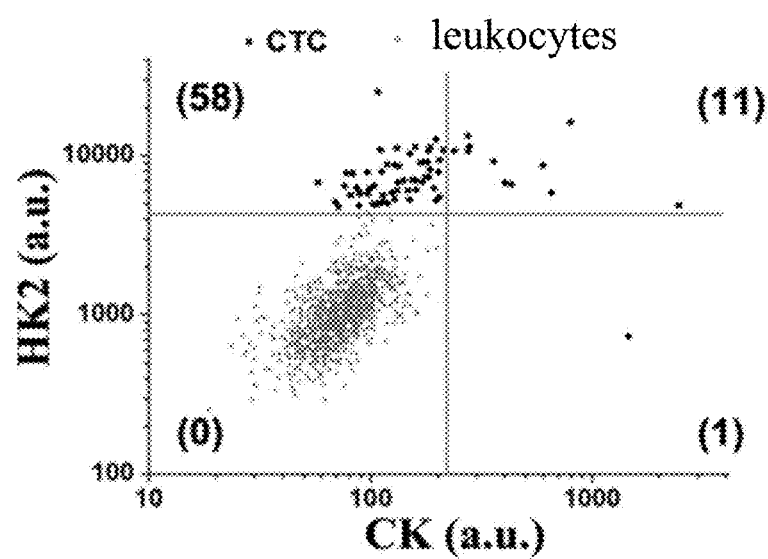
FIG. 3 shows a CTC detection in 5 ml blood sample of one lung adenocarcinoma initial patient, wherein the CD45 negative/DAPI positive/HK2 positive cells are defined as CTC, HK2 and CK positive threshold is mean value of fluorescence values of leucocyte HK2 or CK plus five folds of a standard deviation, the figure marks the number of CTC in four quadrants partitioned by four HK2 and CK positive thresholds.

FIG. 3 shows a CTC detection in 5 ml of lung adenocarcinoma initial patient's blood sample, wherein CD45 negative/DAPI positive/HK2 or CK positive cells are defined as CTC, the figure marks the number of CTC in four quadrants partitioned by four HK2 and CK positive thresholds.

Figure 4:
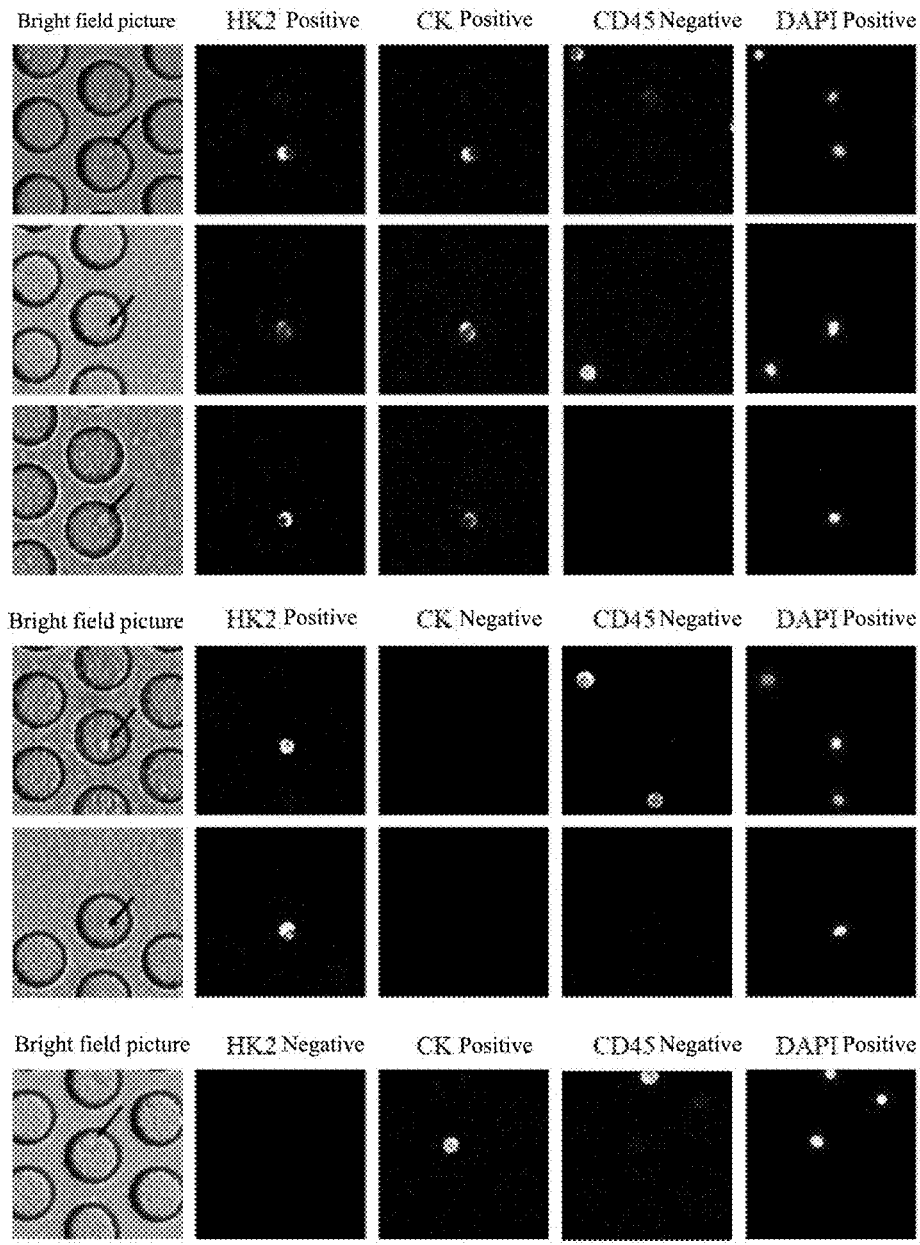

FIG. 4 shows a fluorescent sub-channel diagram of CTC in a lung adenocarcinoma patient related to FIG. 3, according to expression of HK2 and CK, the cells can be further divided into three cell subgroups such as HK2 positive/CK positive/CD45 negative/DAPI positive, HK2 positive/CK negative/CD45 negative/DAPI positive and HK2 negative/CK positive/CD45 negative/DAPI positive and the like.

(9) Target tumor single cell were accurately recycled by means of a micromanipulation platform, and single cell genome-wide amplification was carried out by using commercial kit MALBAC (Yikon Genomics, China). Because there is a mature targeted therapy regime in clinic, BRAF, EGFR and KRAS target gene mutation detection were firstly conducted on the tumor single cell genome-wide amplification product, after the PCR amplification product was confirmed by agarose gel electrophoresis, gene mutation was detected by means of first generation sequencing; the remaining tumor single cell amplification products were used in genome-wide sequencing library construction. The remaining single cell amplification products after the recycling were purified by using 1×Agencourt® AMPure XP beads (Beckman Coulter, USA), the purified nucleic acids were used in genome-wide sequencing library construction, the genome-wide sequencing library construction was carried out by using NEBNext® Ultra™ DNA Library Prep Kit (New England Biolabs, UK), concentration and mass of the sequencing library were evaluated respectively by using Qubite 3.0 (Thermo Fisher Scientific, USA) and Agilent 2100 Bioanalyzer (Agilent, USA), in the genome-wide sequencing HiseqXten (Illumina, USA) sequencing platform was used, and PE150 sequencing strategy was adopted.

Figure 5:
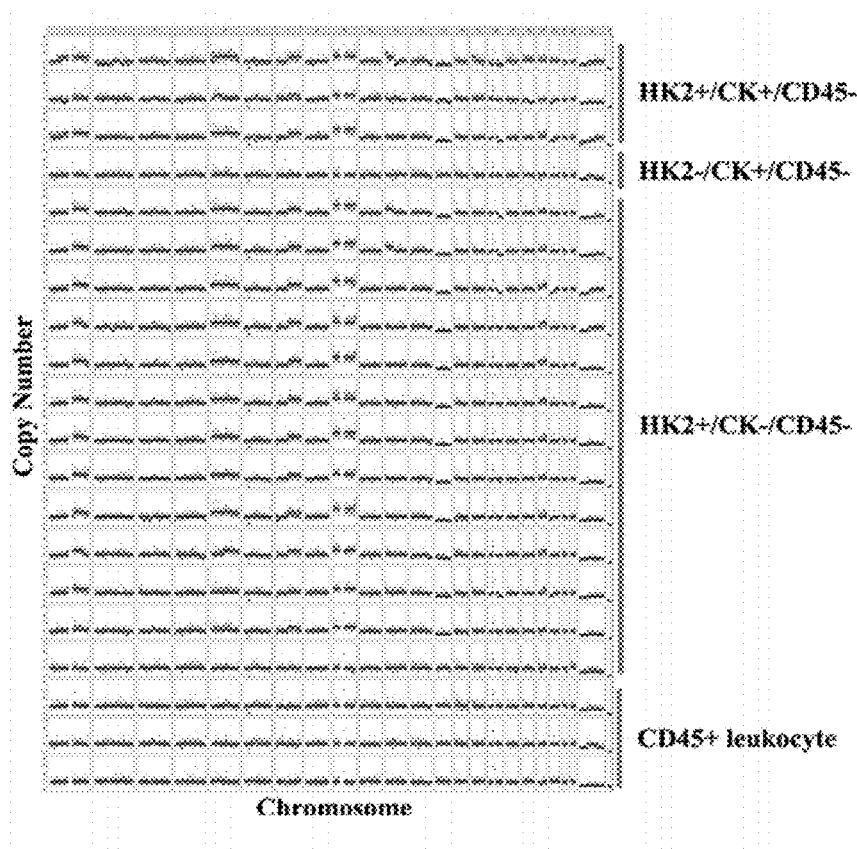
FIG. 5 shows single cell copy number variation detection result of CTC of the lung adenocarcinoma patient related to FIG. 3, this result can confirm that CTC identified based on the HK2 marker are indeed tumor cells.

FIG. 5 shows single cell copy number variation detection result of CTC in the lung adenocarcinoma patient related to FIG. 3, this result confirms that the CTC identified based on HK2 marker are indeed tumor cells.

Results

In all embodiments on the lung adenocarcinoma patient's blood sample, in about 67% of the samples the rare tumor cells were detected. As shown in FIGS. 3 and 4, according to phenotypes of HK2 and CK, these rare tumor cells can be divided into three subgroups: HK2 positive/CK positive/CD45 negative/DAPI positive cell subgroup, HK2 positive/CK negative/CD45 negative/DAPI positive cell subgroup and HK2 negative/CK positive/CD45 negative/DAPI positive cell subgroup.

Figure 6:
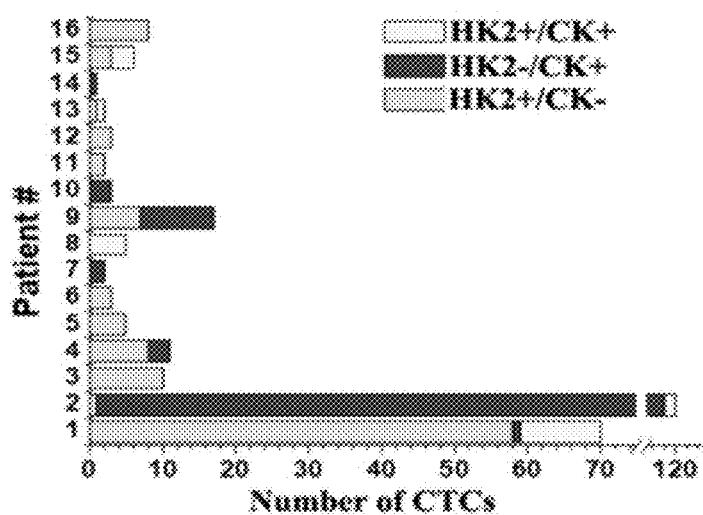
FIG. 6 shows detection results of CTC in bloods of 24 initial lung adenocarcinoma patients and a typing result based on CK expression.

The target single cell were accurately recycled by means of a micromanipulation platform and single cell amplification and sequencing study was conducted for them, the result is as shown in FIG. 5, the HK2 positive/CK positive/CD45 negative/DAPI positive cell subgroup was confirmed as the tumor cell of epithelial origin; the HK2 positive/CK negative/CD45 negative/DAPI positive cell subgroup was the tumor cell which may have epithelial-interstitial transformation; HK2 negative/CK positive/CD45 negative/DAPI positive cells may include the cells of normal epithelial origin and the mesothelial cells, but they are not tumor cells. FIG. 6 shows detection result of CTC in blood of 24 initial lung adenocarcinoma patients and typing result based on CK expression, it is proved that this detection method has high sensitivity and accuracy.

In conclusion, a certain number of target cells were detected in about 67% of the lung adenocarcinoma blood samples, suggesting that sensitivity of this method is high, a validation experiment in which single cell sequencing is conducted on the target cell can show this method also has high accuracy, this method can be used in detecting high glycolysis activity of the circulating tumor cells in a lung adenocarcinoma patient blood, especially it can be used in detecting the circulating tumor cells having epithelial-interstitial transformation in the tumor of epithelial origin, and provide the liquid biopsy of cancer with new detection means and important biological information.

Embodiment 2

Detection of CTC in an Osteosarcoma Patient's Blood Sample

In this embodiment, the method comprises the following steps:

(1) for 5 ml of osteosarcoma patient's peripheral blood sample, CTC were enriched by a method identical to Embodiment 1;

(2) the enriched cell suspension was dripped onto the microporous array chip, standing for 30 minutes making the cells to enter into the micropores, the chip surface was washed twice with HBSS, the solution on the chip surface was absorbed, 100 μl of 2% PFA was added onto the chip and the cells were fixed at room temperature (10 minutes), the chip surface was washed five times with PBS, the solution on the chip surface was absorbed, 30 μl of 0.5% Triton X-100 was added onto the chip and treated for 15 minutes, to increase permeability of cell membrane to the antibody, the chip surface was washed five times with PBS, the solution on the chip surface was absorbed, 100 μl of mixed liquor of 3% BSA and 10% goat serum was added onto the chip, and blocked at room temperature for 1 hour;

(3) the chip surface was washed twice with PBS, the solution on the chip surface was absorbed, 100 μl of antibody mixed liquor was added onto the chip: it includes 1% APC labeled CD45 antibody (source of mouse, Thermo Fisher Company) and 1% HK2 primary antibody (source of the rabbit, Abcam Company), and incubated at 40° C. overnight;

(4) the chip was washed eight times with PBS, the solution on the chip surface was absorbed, 100 µl of mixed liquor of 3% BSA and 10% goat serum was added onto the chip, blocked at room temperature for 1 hour, the chip surface was washed twice with PBS, the solution on the chip surface was absorbed, 100 µl of 0.25% FITC labeled goat anti-rabbit secondary antibody (Thermo Fisher Company) was added onto the chip, incubated at room temperature for 1 hour, the chip was washed five times with PBS, the solution on the chip surface was absorbed, 100 µl of DAPI stock solution was added onto the chip, incubated at room temperature for 10 minutes, after completion of the incubation the chip was washed five times with PBS;

(5) imaged by using the high speed fluorescent imaging equipment, and the scanning result was analyzed, wherein HK2 positive threshold is mean value of the leucocyte fluorescence values on the chip plus five folds of the standard deviation. Criteria for CD45 positive and DAPI positive is if a color is developed then it is positive.

Figure 7:
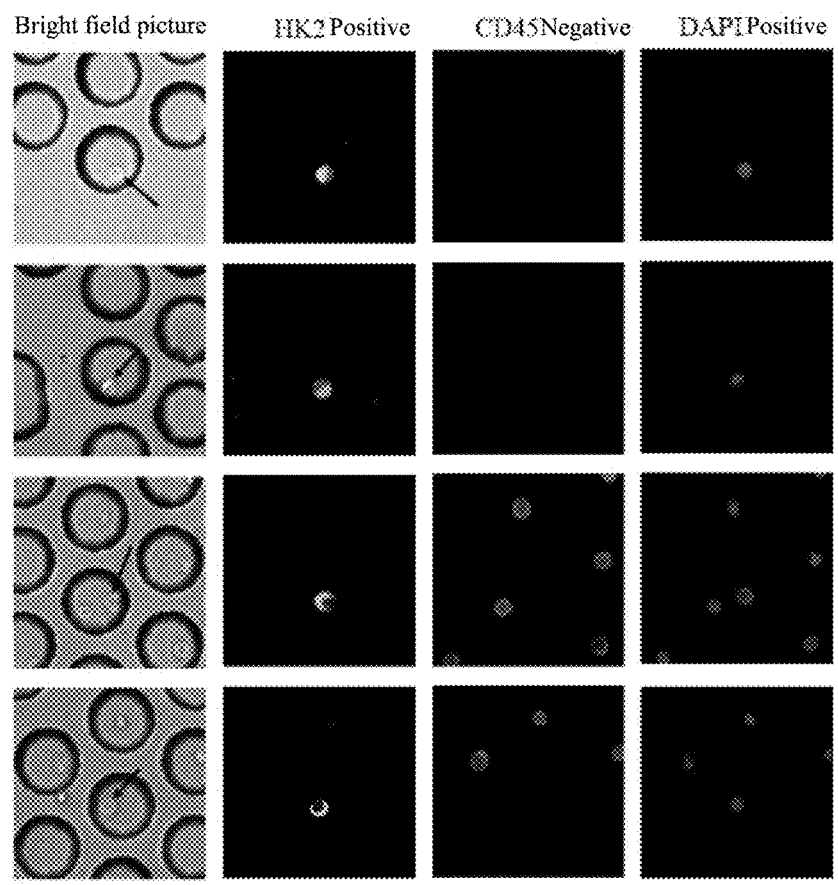
FIG. 7 shows a fluorescent sub-channel diagram of CTC detected in one osteosarcoma patient's blood.

FIG. 7 shows a fluorescent sub-channel diagram of CTC detected in blood of one osteosarcoma patient, wherein CD45 negative/DAPI positive/HK2 positive cells are defined as CTC.

(6) target tumor single cell was accurately recycled by means of the micromanipulation platform, single cell genome-wide amplification was carried out by using commercial kit MALBAC (Yikon Genomics, China). The tumor single cell genome-wide amplification product was directly used in the genome-wide sequencing library construction. The tumor single cell genome-wide amplification product was purified and recycled by using 1×Agencourt® AMPure XP beads (Beckman Coulter, USA), the genome-wide sequencing library construction was carried out by using NEBNext® Ultra™ DNA Library Prep Kit (New England Biolabs, UK), the concentration and mass of the sequencing library were evaluated respectively by using Qubite 3.0 (Thermo Fisher Scientific, USA) and Agilent 2100 Bioanalyzer (Agilent, USA), the genome-wide sequencing was conducted by using Hiseq Xten (Illumina, USA) sequencing platform, and PE150 sequencing strategy was adopted.

Figure 8:
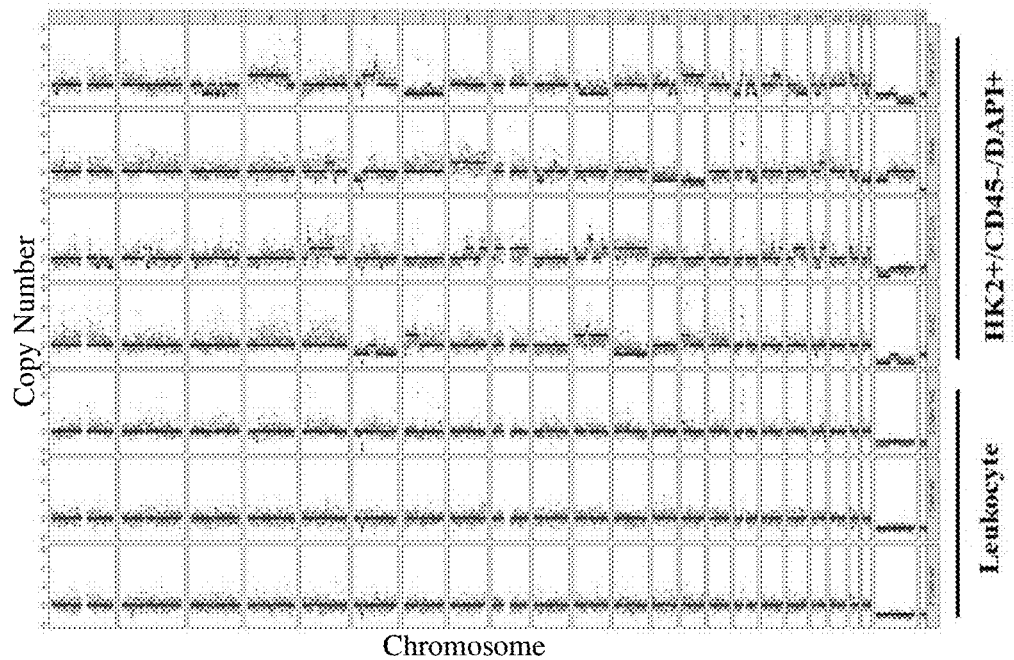
FIG. 8 shows single cell copy number variation detection result of CTC detected in multiple osteosarcoma patients, indicating that HK2 as a marker can detect CTC of a sarcoma having interstitial origin.

FIG. 8 shows single cell copy number variation detection result of CTC detected in multiple osteosarcoma patients, it is confirmed that CTC identified based on HK2/CD45/DAPI marker combination are indeed tumor cells, this indicates that HK2/CD45/DAPI as a marker combination can be used in detecting CTC of sarcoma having interstitial origin.

Results

For 70 osteosarcoma patient's peripheral blood samples, a certain amount of HK2 positive/CD45 negative/DAPI positive rare tumor cells were found in 48 samples. The target single cells were accurately recycled by means of the micromanipulation platform and a single cell amplification and sequencing study was conducted for it, the results are as shown in FIG. 8, HK2 positive/CD45 negative/DAPI positive cells are confirmed as CTC, suggesting that this method has high sensitivity and accuracy, being suitable in detecting the circulating tumor cells of the tumor having interstitial origin.

Embodiment 3

Detection of Rare Tumor Cells in a Lung Cancer Patient's Cerebrospinal Fluid Sample In this embodiment, the method comprises the following steps:

(1) 5 ml of lung cancer brain metastases patient's cerebrospinal fluid sample was taken, centrifuged (300 g, 5 minutes), the vast majority of the supernatant was discarded, the cells were resuspended with the remaining 100 µl of supernatant, this 100 µl of cell suspension was dripped onto the microporous array chip, standing for 10 minutes making the cells to enter into the micropores;

(2) the chip surface was washed twice with HBSS, the solution on the chip surface was absorbed, 100 µl of 2% PFA was added onto the chip, the cells were fixed at room temperature (10 minutes), the chip surface was washed five times with PBS, the solution on the chip surface was absorbed, 30 µl of 0.5% Triton X-100 was added onto the chip and treated for 15 minutes, to increase permeability of cell membrane to the antibody, the chip surface was washed five times with PBS, the solution on the chip surface was absorbed, 100 µl of mixed liquor of 3% BSA and 10% goat serum was added onto the chip, and blocked at room temperature for 1 hour;

(3) the chip surface was washed twice with PBS, the solution on the chip surface was absorbed, 100 µl of antibody mixed liquor was added onto the chip: it includes 1% APC labeled CD45 antibody (source of mouse, Thermo Fisher Company), 1% PE labeled CK antibody (source of mouse, BD Company) and 1% HK2 primary antibody (source of rabbit, Abcam Company), and incubated at 40° C. overnight;

(4) the chip was washed eight times with PBS, the solution on the chip surface was absorbed, 100 µl of mixed liquor of 3% BSA and 10% goat serum was added onto the chip, blocked at room temperature for 1 hour, the chip surface was washed twice with PBS, the solution on the chip surface was absorbed, 100 µl of 0.25% FITC labeled goat anti-rabbit secondary antibody (Thermo Fisher Company) was added onto the chip, incubated at room temperature for 1 hour, the chip was washed five times with PBS, the solution on the chip surface was absorbed, 100 µl of DAPI stock solution was added onto the chip, incubated at room temperature for 10 minutes, after completion of the incubation the chip was washed with PBS five times;

(5) imaged by using the high speed fluorescent imaging equipment, and the scanning result was analyzed, wherein HK2 and CK positive threshold is mean value of the leucocyte fluorescence values on the chip plus five folds of the standard deviation. Criteria for CD45 positive and DAPI positive is if a color is developed then it is positive.

Figure 9:
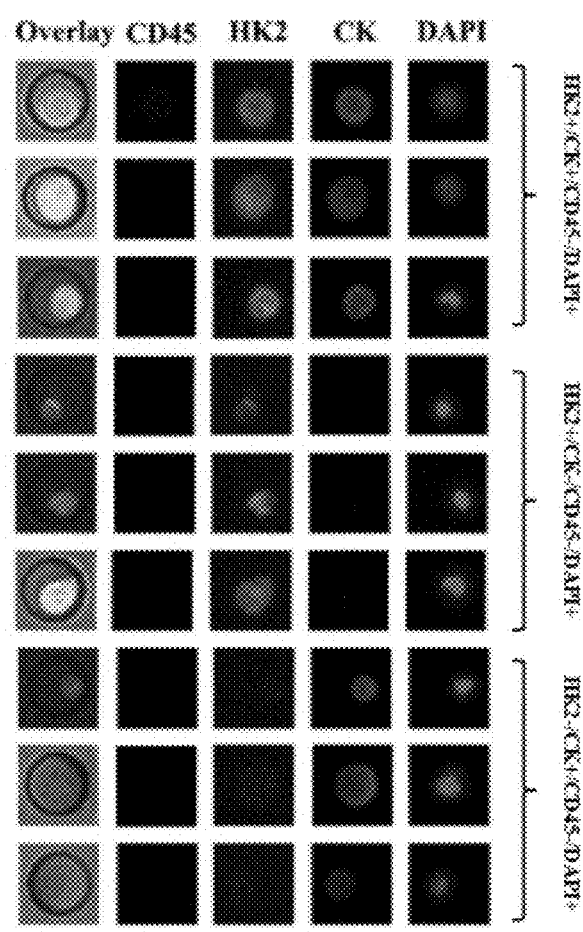

FIG. 9 shows a fluorescent subchannel diagram of the rare tumor cells detected in 5 ml of cerebrospinal fluid sample of one lung adenocarcinoma patient, according to expression of HK2 and CK the cells can further be divided into three cell subgroups such as HK2 positive/CK positive/CD45 negative/DAPI positive, HK2 positive/CK negative/CD45 negative/DAPI positive and HK2 negative/CK positive/CD45 negative/DAPI positive and the like.

(6) The target tumor single cell was accurately recycled by means of the micromanipulation platform, a single cell genome-wide amplification was carried out by using commercial kit MALBAC (Yikon Genomics, China). Because there are mature targeted therapy regimes in clinic, BRAF, EGFR and KRAS target gene mutation detections were firstly conducted on the tumor single cell genome-wide amplification product, after the PCR amplification product was confirmed by agarose gel electrophoresis, the gene mutation was detected by means of the first generation sequencing; the remaining tumor single cell amplification products were used in genome-wide sequencing library construction. The remaining single cell amplification products were purified and recycled by using 1×Agencourt® AMPure XP beads (Beckman Coulter, USA), the purified nucleic acids were used in genome-wide sequencing library construction, the genome-wide sequencing library construction was carried out by using NEBNext® UltrarM DNA Library Prep Kit (New England Biolabs, UK), the concentration and mass of the sequencing library were respectively evaluated by using Qubite 3.0 (Thermo Fisher Scientific, USA) and Agilent 2100 Bioanalyzer (Agilent, USA), a genome-wide sequencing was conducted by using Hiseq Xten (Illumina, USA) sequencing platform, and PE150 sequencing strategy was adopted.

Figure 10:
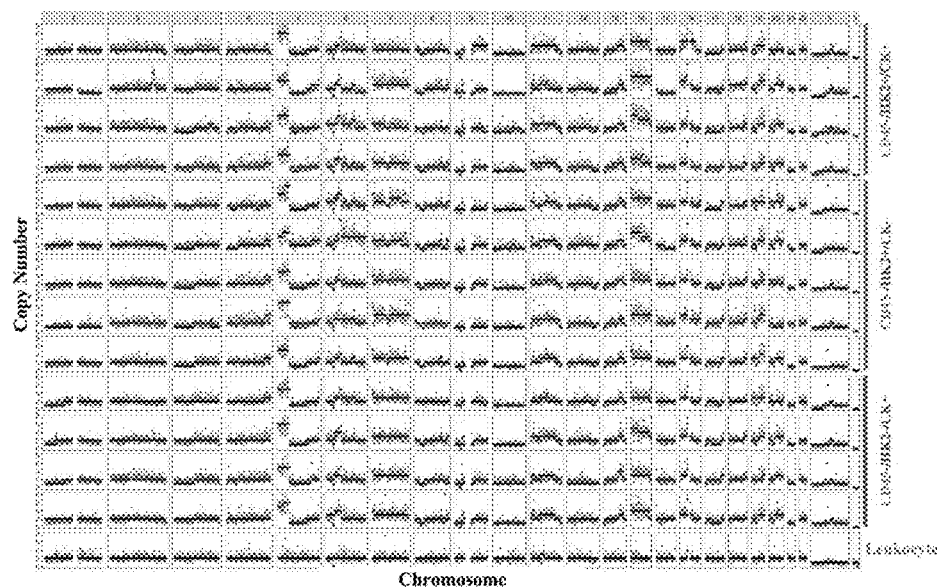
FIG. 10 shows single cell copy number variation detection result of rare tumor cells in cerebrospinal fluid of one lung adenocarcinoma patient related to FIG. 9, it can be confirmed that the rare tumor cells identified based on the HK2 marker are tumor cells.

FIG. 10 shows single cell copy number variation detection result of the rare tumor cells in the lung adenocarcinoma patient's cerebrospinal fluid related to FIG. 9, it is proved that the rare tumor cells identified based on HK2/CD45/DAPI marker combination are all tumor cells.

Results

In a lung cancer patient's cerebrospinal fluid sample experiment, rare tumor cells were detected in all the samples, according to HK2 and CK of phenotype, these rare tumor cells can be divided into three subgroups: HK2 positive/CK positive/CD45 negative/DAPI positive cell subgroup, HK2 positive/CK negative/CD45 negative/DAPI positive cell subgroup and HK2 negative/CK positive/CD45 negative/DAPI positive cell subgroup.

The target single cell was accurately recycled by means of the micromanipulation platform and single cell amplification and sequencing study was conducted, the results are as shown in FIG. 10, the HK2 positive/CK positive/CD45 negative/DAPI positive cell subgroup are tumor cells having epithelial origin; HK2 positive/CK negative/CD45 negative/DAPI positive cell subgroup may be tumor cells having epithelial-interstitial transformation; HK2 negative/CK positive/CD45 negative/DAPI positive cell subgroup may be tumor cells having low glycolysis of epithelial origin, suggesting that this method has high sensitivity and reliability, it can be used in detecting the rare tumor cells having high glycolysis activity in the lung adenocarcinoma patient's cerebrospinal fluid sample, especially it can be used in detecting the rare tumor cells having epithelial-interstitial transformation in the tumor of epithelial origin.

Embodiment 4

Detection of Rare Tumor Cells in a Lung Cancer Patient Hydrothorax Sample

In this embodiment, the method comprises the following steps:

(1) 10 ml of lung cancer patient's hydrothorax was centrifuged (300 g, 5 minutes) and the cells were isolated, 5 ml of erythrocyte lysate (BD Company) was added and lysed in a dark place for 5 minutes, centrifuged again (300 g, 5 minutes), after the supernatant was discarded, the cells were resuspended with HBSS and washed, centrifuged (300 g, 5 minutes) and the supernatant was discarded, 1 ml of HBSS resuspended cell was added;

(2) the obtained cell suspension was dripped onto the addressable microporous array chip, standing for 10 minutes, making the cell to enter into the micropores;

(3) the chip surface was washed twice with HBSS, the solution on the chip surface was absorbed, 100 µl of 2% PFA was added onto the chip and the cells were fixed at room temperature (10 minutes), the chip surface was washed five times with PBS, the solution on the chip surface was absorbed, 30 µl of 0.5% Triton X-100 was added onto the chip and treated for 15 minutes, to increase permeability of cell membrane to the antibody, the chip surface was washed five times with PBS, the solution on the chip surface was absorbed, 100 µl of a mixed liquor of 3% BSA and 10% goat serum was added onto the chip, and blocked at room temperature for 1 hour;

(4) the chip surface was washed twice with PBS, the solution on the chip surface was absorbed, 100 µl of antibody mixed liquor was added onto the chip: it includes 1% APC labeled CD45 antibody (source of mouse, Thermo Fisher Company), 1% PE labeled CK antibody (source of mouse, BD Company) and 1% HK2 primary antibody (source of rabbit, Abcam Company), and incubated at 40° C. overnight;

(5) the chip was washed eight times with PBS, the solution on the chip surface was absorbed, 100 µl of mixed liquor of 3% BSA and 10% goat serum was added onto the chip, blocked at room temperature for 1 hour, the chip surface was washed twice with PBS, the solution on the chip surface was absorbed, 100 µl of 0.25% FITC labeled goat anti-rabbit secondary antibody (Thermo Fisher Company) was added onto the chip, incubated at room temperature for 1 hour, the chip was washed five times with PBS, the solution on the chip surface was absorbed, 100 µl of DAPI stock solution was added onto the chip, and incubated at room temperature for 10 minutes, after completion of the incubation the chip was washed five times with PBS;

(6) imaged by using the high speed fluorescent imaging equipment, and the scanning result was analyzed, wherein HK2 and CK positive threshold is mean value of leucocyte fluorescence values on the chip plus five folds of the standard deviation. Criteria for CD45 positive and DAPI positive is if a color is developed then it is positive.

Figure 11:
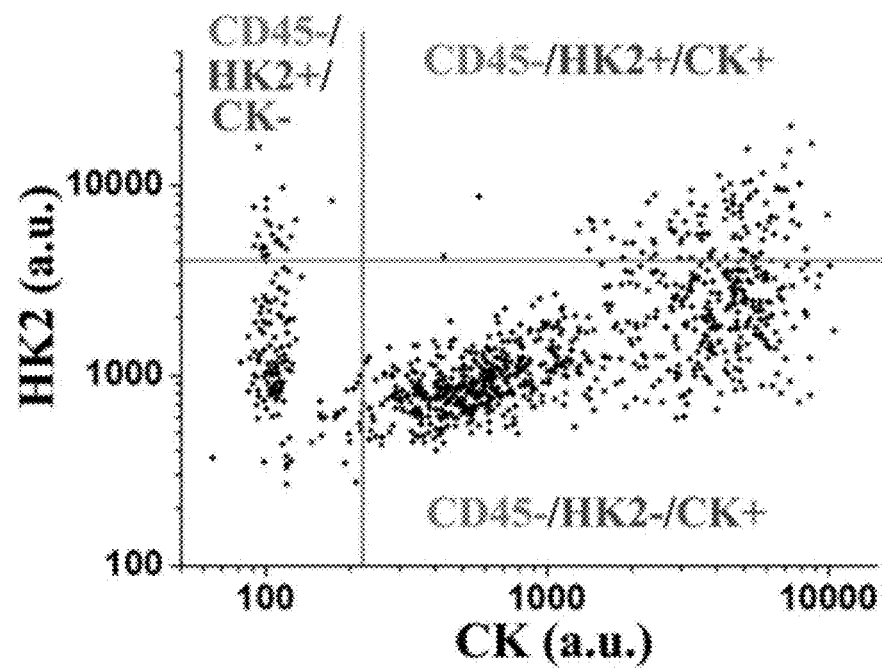
FIG. 11 shows a detection of rare tumor cells in hydrothorax sample of one lung adenocarcinoma patient, wherein CD45 negative/DAPI positive/HK2 positive cells are defined as the rare tumor cells, HK2 and CK positive threshold is mean value of the leucocyte fluorescence values plus five folds of the standard deviation.

FIG. 11 shows detection of the rare tumor cells in one lung adenocarcinoma patient's hydrothorax sample, wherein CD45 negative/DAPI positive/HK2 or CK positive cells are defined as rare tumor cells.

Figure 12:
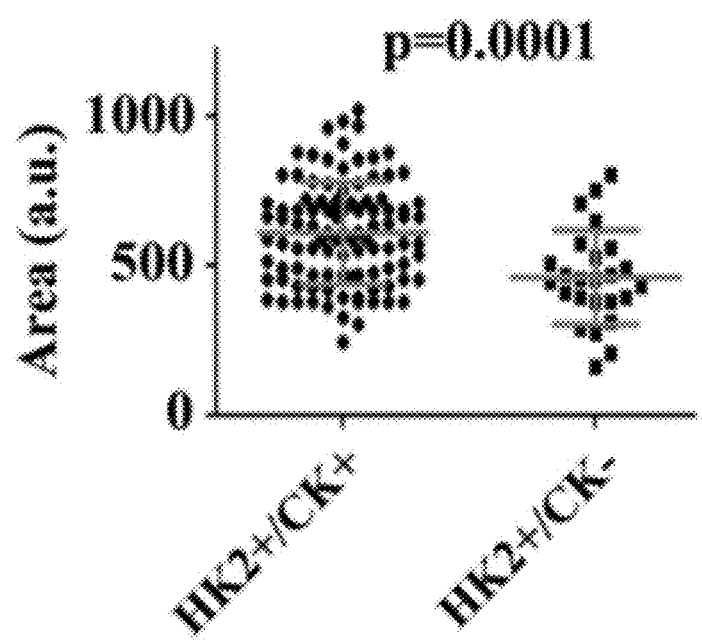
FIG. 12 shows a size comparison of HK2 positive/CK positive rare tumor cells with HK2 positive/CK negative rare tumor cells in the lung adenocarcinoma patient's hydrothorax related to related to FIG. 11, wherein the size is measured by using absolute area of the cells on a fluorescent scanning picture.

FIG. 12 shows a size comparison of HK2 positive/CK positive rare tumor cells in the lung adenocarcinoma patient's hydrothorax related to FIG. 11 with HK2 positive/CK negative rare tumor cells, wherein the size is measured by using absolute area of the cells on a fluorescent scanning picture.

(7) The target tumor single cell was accurately recycled by means of the micromanipulation platform, a single cell genome-wide amplification was carried out by using commercial kit MALBAC (Yikon Genomics, China). Because there is mature targeted therapy regime in clinic, BRAF, EGFR and KRAS target gene mutation detections were firstly conducted on the tumor single cell genome-wide amplification product, after the PCR amplification product was confirmed by agarose gel electrophoresis, the gene mutation was detected by means of the first generation sequencing; the remaining tumor single cell amplification products were used in the genome-wide sequencing library construction. The remaining single cell amplification products after recycling were purified by using 1×Agencourt® AMPure XP beads (Beckman Coulter, USA), the purified nucleic acids were used in of genome-wide sequencing library construction, the genome-wide sequencing library construction was carried out by using NEBNext® Ultra™ DNA Library Prep Kit (New England Biolabs, UK), the concentration and mass of the sequencing library were evaluated respectively by using Qubite 3.0 (Thermo Fisher Scientific, USA) and Agilent 2100 Bioanalyzer (Agilent, USA), a genome-wide sequencing was conducted by using Hiseq Xten (Illumina, USA) sequencing platform, and PE150 sequencing strategy was adopted.

Figure 13:
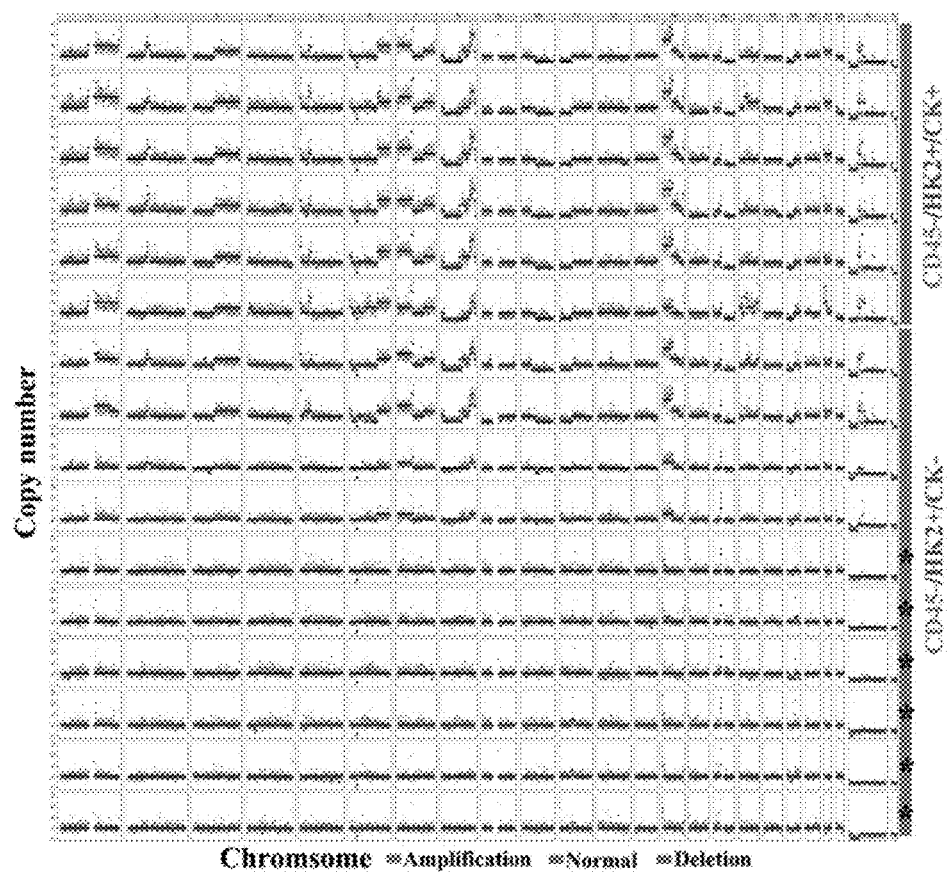
FIG. 13 shows single cell copy number variation detection result of rare tumor cells in the lung adenocarcinoma patient's hydrothorax related to FIG. 11, through a single cell sequencing, the cells shown in the figure all have EGFR L858R driver mutation, therefore they are all tumor cells, but wherein the single cell copy number variation characteristics of the tumor cells of HK2 positive/CK positive and HK2 positive/CK negative are different.

FIG. 13 shows single cell copy number variation detection result of the rare tumor cells in the lung adenocarcinoma patient's hydrothorax related to FIG. 11, on the basis of the single cell sequencing, the cells shown in the figure all have EGFR L858R driver mutation, thus they are all tumor cells, but wherein the single cell copy number variation characteristics of CK positive and CK negative tumor cells are different.

Figure 14:
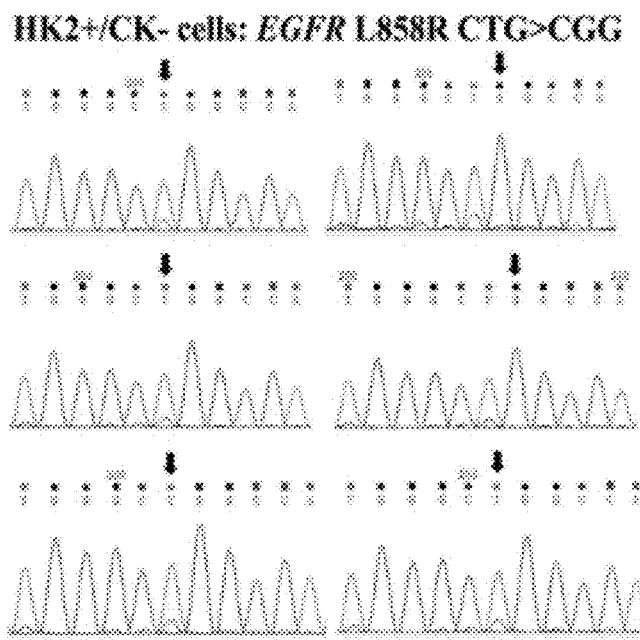
FIG. 14 shows a Sanger sequencing diagram of six asterisked cells in FIG. 13, showing that the six cells carry the EGFR L858R mutation, they can be conformed as tumor cells.

FIG. 14 shows a Sanger sequencing diagram of six asterisked cells in FIG. 13, showing that the six cells all carry the EGFR L858R mutation, they can be indeed tumor cells.

Embodiment 5

Detection of Rare Tumor Cells in a Bladder Cancer Patient Urine Sample

In this embodiment, the method comprises the following steps:

(1) a urine sample was centrifuged (4° C., 410 g, 5 minutes, centrifuge braking: acceleration 8, deceleration 8), the supernatant was discarded, and an appropriate amount of Healthsky diluent resuspended cells were added;

(2) 2 ml of cell suspension was taken and added into a funnel of a slide sheet producing bin, a slide was put into the sheet producing machine, centrifuged (4° C., 200 g, 3 minutes), the liquid in the sheet producing bin was thrown away, and the slide was rinsed with a tap water;

(3) the sheet producing bin was rotated and removed, the slide was taken out, rinsed for a few seconds with the tap water, immediately immersed into 95% ethanol and fixed for 15 minute, soaked in a running tap water for 1 minute, the slide was taken out, the cells were kept in a liquid environment, the surrounding excess water was wiped away, a range was drawn with a Super Pap Pen;

(4) the liquid was absorbed away, 50 µl of 0.5% Triton X-100 was added and treated 15 minutes, to increase permeability of cell membrane to the antibody, and washed four times with PBS, 100 µl of mixed liquor of 3% BSA and 10% goat serum was added, blocked at room temperature for 1 hour, washed twice with PBS, and 100 µl of antibody mixed liquor was added: it includes 1% APC labeled CD45 antibody (source of mouse, Thermo Fisher Company) and 1% HK2 primary antibody (source of rabbit, Abcam Company), and incubated at 4° C. overnight;

(5) washed five times with PBS, 100 µl of mixed liquor of 3% BSA and 10% goat serum was added, blocked at room temperature for 1 hour, washed twice with PBS, the surface solution was absorbed away, 100 µl of 0.25% FITC labeled goat anti-rabbit secondary antibody (Thermo Fisher Company) was added, incubated at room temperature for 1 hour, washed five times with PBS, the surface solution was absorbed away, 100 µl of DAPI stock solution was added, incubated at room temperature for 10 minutes, after completion of the incubation washed five times with PBS;

(6) imaged by using the high speed fluorescent imaging equipment, and the scanning result was analyzed, wherein HK2 positive threshold is mean value of the leucocyte fluorescence values on the chip plus five folds of the standard deviation. Criteria for CD45 positive and DAPI positive is if a color is developed then it is positive.

(7) the target tumor single cells (namely HK2 positive, CD45 negative, DAPI positive) was accurately recycled by means of the micromanipulation platform, single cell genome-wide amplification was carried out by using commercial kit MALBAC (Yikon Genomics, China). The tumor single cell genome-wide amplification products were directly used in the genome-wide sequencing library construction. The tumor single cell genome-wide amplification products were purified and recycled by using 1×Agencourt® AMPure XP beads (Beckman Coulter, USA), the genome-wide sequencing library construction was carried out by using NEBNext® Ultra™ DNA Library Prep Kit (New England Biolabs, UK), concentration and mass of the sequencing library were evaluated respectively by using Qubite 3.0 (Thermo Fisher Scientific, USA) and Agilent 2100 Bioanalyzer (Agilent, USA), the genome-wide sequencing was conducted by using HiseqXten (Illumina, USA) sequencing platform, and PE150 sequencing strategy was adopted.

Figure 15:
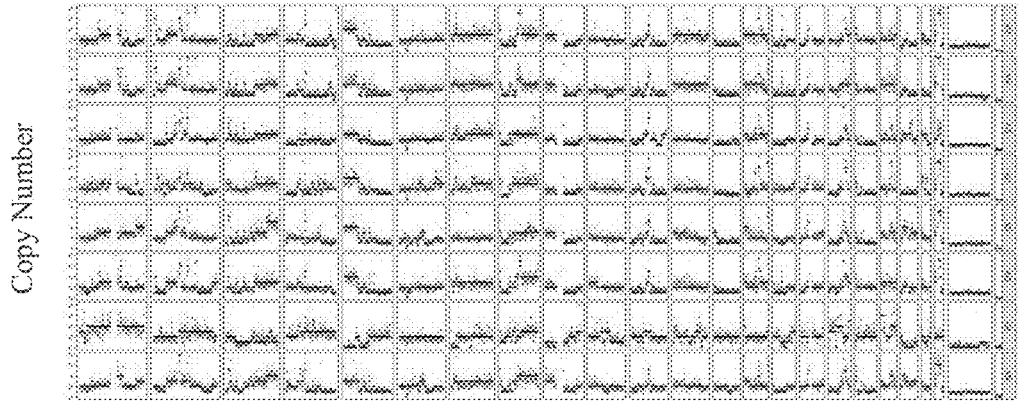
FIG. 15 shows single cell copy number variation detection result of rare tumor cells detected in a bladder cancer patient's urine, and confirms that the rare tumor cells identified based on the HK2 marker are tumor cells.

FIG. 15 shows single cell copy number variation detection result of rare tumor cells in a bladder cancer patient's urine, it can be confirmed that the rare tumor cells identified based on HK2 marker high expression are tumor cells.

Results

In a bladder cancer patient's urine sample experiment, the rare tumor cells were detected in all the samples, the target single cells was accurately recycled by means of the micromanipulation platform and a single cell amplification and sequencing study was conducted, the results are as shown in FIG. 15, HK2 positive/CD45 negative/DAPI positive cell was confirmed as tumor cells.

In conclusion, it is suggested the method has high sensitivity and reliability, it can be used in detecting the rare tumor cells having high glycolysis activity in a bladder cancer patient's urine sample.

The above-described are only preferred embodiments of the present application. It should be noted that, a person skilled in the art can also make several improvements and complements without departing from the method according to the present application, these improvements and complements should also be regarded as the protection scope of the present application.

What is claimed is:

1. A method for detecting circulating tumor cells in a human body fluid sample, comprising:
   incubating the human body fluid sample with a fluorescein labeled hexokinase-2 (HK2) antibody, an antibody specific to a leukocyte marker, and a cell nucleus stain;
   measuring the level of fluorescein labeled HK2 antibody bound to cells in the human body fluid sample that are stained by the cell nucleus stain, and are not bound to the antibody specific to the leukocyte marker; and
   identifying cells that are bound to a level of fluorescein labeled HK2 antibody higher than the mean plus five times of standard deviation of reference HK2 antibody levels bound to leukocytes as circulating tumor cells.

2. The method according to claim 1, wherein the fluorescein labeled HK2 antibody is a fluorescein labeled HK2 antibody, or a HK2 antibody bound to a fluorescein labeled secondary antibody targeting the HK2 antibody.

3. The method according to claim 1, wherein the leukocyte marker is cell membrane surface protein CD45.

4. The method according to claim 1, wherein the human body fluid sample is selected from the group consisting of blood, pleural effusion, cerebrospinal fluid and urine.

* * * * *